United States Patent [19]
Siegel et al.

[11] Patent Number: 5,209,909
[45] Date of Patent: May 11, 1993

[54] TWO COMPARTMENT CUP FOR POWDERED STERILANT REAGENT COMPONENTS

[75] Inventors: Norman L. Siegel, Mentor; Raymond C. Kralovic, Ashtabula; Kenneth E. Scheckelhoff, Mentor, all of Ohio

[73] Assignee: Steris Corporation, Mentor, Ohio

[21] Appl. No.: 793,589

[22] Filed: Nov. 18, 1991

Related U.S. Application Data

[63] Continuation-in-part of Ser. No. 681,118, Apr. 5, 1991, and Ser. No. 342,189, Apr. 24, 1989, Pat. No. 5,116,575, which is a continuation-in-part of Ser. No. 229,917, Aug. 8, 1988, Pat. No. 5,077,008, which is a continuation-in-part of Ser. No. 165,189, Mar. 17, 1988, Pat. No. 5,037,623, and Ser. No. 140,388, Jan. 4, 1988, Pat. No. 4,892,706, said Ser. No. 165,189, and Ser. No. 140,388, each is a continuation-in-part of Ser. No. 826,730, Feb. 6, 1986, Pat. No. 4,731,222, said Ser. No. 681,118, is a continuation-in-part of Ser. No. 342,189, Feb. 6, 1986, and Ser. No. 349,304, May 9, 1989, Pat. No. 5,091,343, which is a continuation-in-part of Ser. No. 140,388, May 9, 1989.

[51] Int. Cl.[5] ............................................. A61L 2/18
[52] U.S. Cl. ................................ 422/292; 206/219; 206/538; 422/102; 422/294
[58] Field of Search ................ 422/102, 292, 294; 206/219, 538

[56] References Cited

U.S. PATENT DOCUMENTS

2,494,456  1/1950  Still .................................. 206/219 X
4,171,340 10/1979  Nishimura et al. .................... 422/36
4,482,047 11/1984  Ackermann et al. ................ 206/219
4,483,439 11/1984  Steigerwald et al. ............... 206/219

Primary Examiner—Jill A. Johnston
Attorney, Agent, or Firm—Fay, Sharpe, Beall, Fagan, Minnich & McKee

[57] ABSTRACT

A front door (B) of a countertop decontamination unit is opened to gain access to a chamber (10) for receiving a cartridge (C) containing items to be sterilized and a chamber (12) for receiving a two compartment powdered anti-microbial agent carrying cup (D). The cup includes an outer cup portion (60) and an inner cup portion (70) that have peripheral walls (62, 72) affixed together at flanges (64, 74) and abutting base walls (66, 76). At least one of the base walls has a domed portion (68) constructed of plastic, whose plastic resiliency functions as a spring to urge the base walls continuously into engagement. The inner and outer cup portions peripheral walls define an annular chamber (86) therebetween. Preferably, the inner peripheral wall is generally conical to reinforce the outer cup base wall to prevent it from collapsing on impact with a cutting blade (14). The inner wall has a longitudinally elongated recess (80) which interacts with a filling aperture (84) surrounded by a flange portion (82). The longitudinal recess and filling aperture are configured such that a filling tube (92) is selectively insertable through the filling aperture and along the recess for filling the annular compartment with a powdered reagent. A permeable sheet (102) is affixed to the second cup portion flange for sealing both compartments.

22 Claims, 5 Drawing Sheets

TWO COMPARTMENT CUP FOR POWDERED STERILANT REAGENT COMPONENTS

This application is a continuation-in-part of U.S. application Ser. Nos. 07/681,118, filed Apr.5, 1991 and 07/342,189, now U.S. Pat. No. 5,116,575, filed Apr. 24, 1989.

U.S. application Ser. No. 07/681,118, is a continuation-in-part of U.S. application Ser. No. 349,304, filed May 9, 1989, now U.S. Pat. No. 5,091,343, and said U.S. application Ser. No. 07/342,189. U.S. application Ser. No. 349,304 is a continuation-in-part of U.S. application Ser. No. 140,388, filed Jan. 4, 1988, now U.S. Pat. No. 4,892,706. U.S. application Ser. No. 07/342,189 is a continuation-in-part of U.S. application Ser. No. 229,917, filed Aug. 8, 1988, now U.S. Pat. No. 5,077,088, which is a continuation-in-part of said U.S. application Ser. Nos. 140,388 and 07/165,189, now U.S. Pat. No. 5,037,623, filed Mar. 17, 1988, which in turn are continuations-in-part of U.S. application Ser. No. 826,730, filed Feb. 6, 1986, now U.S. Pat. No. 4,731,222.

BACKGROUND OF THE INVENTION

The present invention relates to the decontamination art. It finds particular application in conjunction with sterilizing or disinfecting medical instruments and equipment and will described with particular reference thereto. It will be appreciated, however, that the invention is also applicable to a wide variety of technologies in which at least two components or reagents are kept separate until time of use and then mechanically released.

Decontamination connotes the removal of hazardous or unwanted materials, such as bacteria, mold spores, other pathogenic life forms, radioactive dust, and the like. Disinfection connotes the absence of pathogenic life forms. Sterilization connotes the absence of all life forms, whether pathogenic or not.

Heretofore, medical equipment and instruments have often been sterilized in a steam autoclave. Autoclaves kill life forms with a combination of high temperature and pressure. However, steam autoclaves have several drawbacks. The high temperature pressure vessels tend to be bulky and heavy. The high temperature and pressure tends to curtail the useful life of the endoscopes, rubber and plastic devices, lenses, and portions of devices made of polymeric materials and the like. Moreover, the autoclave sterilizing and cool down cycle is sufficiently long, that multiple sets of the medical instruments are commonly required.

Instruments which cannot withstand the pressure or temperature of the oven autoclave are often sterilized with ethylene oxide gas, particularly in larger medical facilities or hospitals. However, the ethylene oxide sterilization technique also has several drawbacks. First, the ethylene oxide sterilization cycle is even longer than the steam autoclave cycle. Another drawback is that ethylene oxide sterilization is sufficiently sophisticated that trained technicians are commonly required, making it unsuitable for physician and dental offices and for other smaller medical facilities. Yet another drawback is that some medical equipment can not be sterilized with ethylene oxide gas.

Liquid sterilization systems have also been utilized for equipment which could not withstand the high temperatures of steam sterilization. Commonly, a technician mixes a liquid sterilant composition and manually immerses the items to be sterilized. The high degree of manual labor introduces numerous uncontrolled and unreported variables into the sterilization process. There are quality assurance problems with the weakening of the sterilants due to aging on the shelf, technician error in the mixing of sterilants, technician error in the control of the immersion times, technician error between immersion and the rinsing of residue, technician errors in the rinsing of the residue, exposure to the ambient atmosphere after the rinsing step, and the like.

In the applicant's prior automated liquid sterilization systems described in the above-referenced parent applications, a relatively rigid, strong plastic container holds a liquid paracetic acid sterilant. The liquid sterilant container is supported in an upper half of a lighter weight plastic cup which holds powdered buffers, corrosion inhibitors, wetting agents, and other reagents in the lower half. The entire assembly is received in the automated equipment. Both containers are severed concurrently by a knife blade(s) that is driven through the bottom of the lightweight container, through the powdered reagents, to the more rigid liquid reagent filled container. Although successful, the use of liquid reagents complicates shipping and handling of the sterilant concentrate, particularly the venting required by paracetic acid.

The present invention provides for a new and improved two compartment cup or packaging assembly which is ideal for storing powdered reagents which are retained separately until time of use.

SUMMARY OF THE INVENTION

In accordance with the present invention, a two compartment package is provided. An outer container has a peripheral side wall which is connected with a base wall at a first end and open at a second end. A second cup portion has a flange which is supported by the first cup open end, a smaller circumferentially peripheral wall extending from the flange to a second cup base wall which abuts the first cup base wall. In this manner, an annular chamber is defined between the first and second cup peripheral walls. A cover is sealed to the second cup flange.

In accordance with a more specific aspect of the present invention, the second cup peripheral wall has a recess therein which meets with a corresponding aperture in its peripheral flange to define a path between the first and second cups for filling the annular chamber between the peripheral walls.

In accordance with another more specific aspect of the present invention, the bottom walls of the first and second cups abut. At least one of the bottom walls is domed toward the other. The cups are dimensioned such that, as the first and second cups are mated together, the bottom walls engage flexing the dome. In this manner, the dome provides a spring bias to urge the two base walls together.

In accordance with a more limited aspect of the present invention, the inner cup is substantially conical to reinforce the second cup bottom wall. This inhibits a cutting knife from collapsing the outer cup without severing it.

In accordance with another more limited aspect of the present invention, the inner cup flange extends peripherally around the second cup and the filling opening. The outer cover is sealed to the inner cup flange sealing both the inner cup and fill spout to the annular chamber between the cups concurrently.

In accordance with another aspect of the present invention, the closure is semi-permeable to permit one or both reagents to outgas.

In accordance with yet another aspect of the present invention, the inner cup and the annular chamber are filled with powdered reagents which interact in water to form a strong oxidant and corrosion inhibitors.

In accordance with a more limited aspect of the present invention, one of the annular chamber and the inner cup holds a powdered, water soluble acid precursor and the other holds a powdered borate, other powdered corrosion inhibitors, and a powdered wetting agent.

One advantage of the present invention is that it facilitates materials handling.

Another advantage of the present invention is that it simplifies filling and sealing of two reagents in separate compartments.

Another advantage of the present invention is that it inhibits failure of a mechanical cutting operation by inhibiting collapsing of the package upon interaction with a moving cutting blade.

Another advantage of the present invention is that it facilitates the handling and shipping of reagents which interact in water to form a strong anti-microbial solution.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangements of components and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
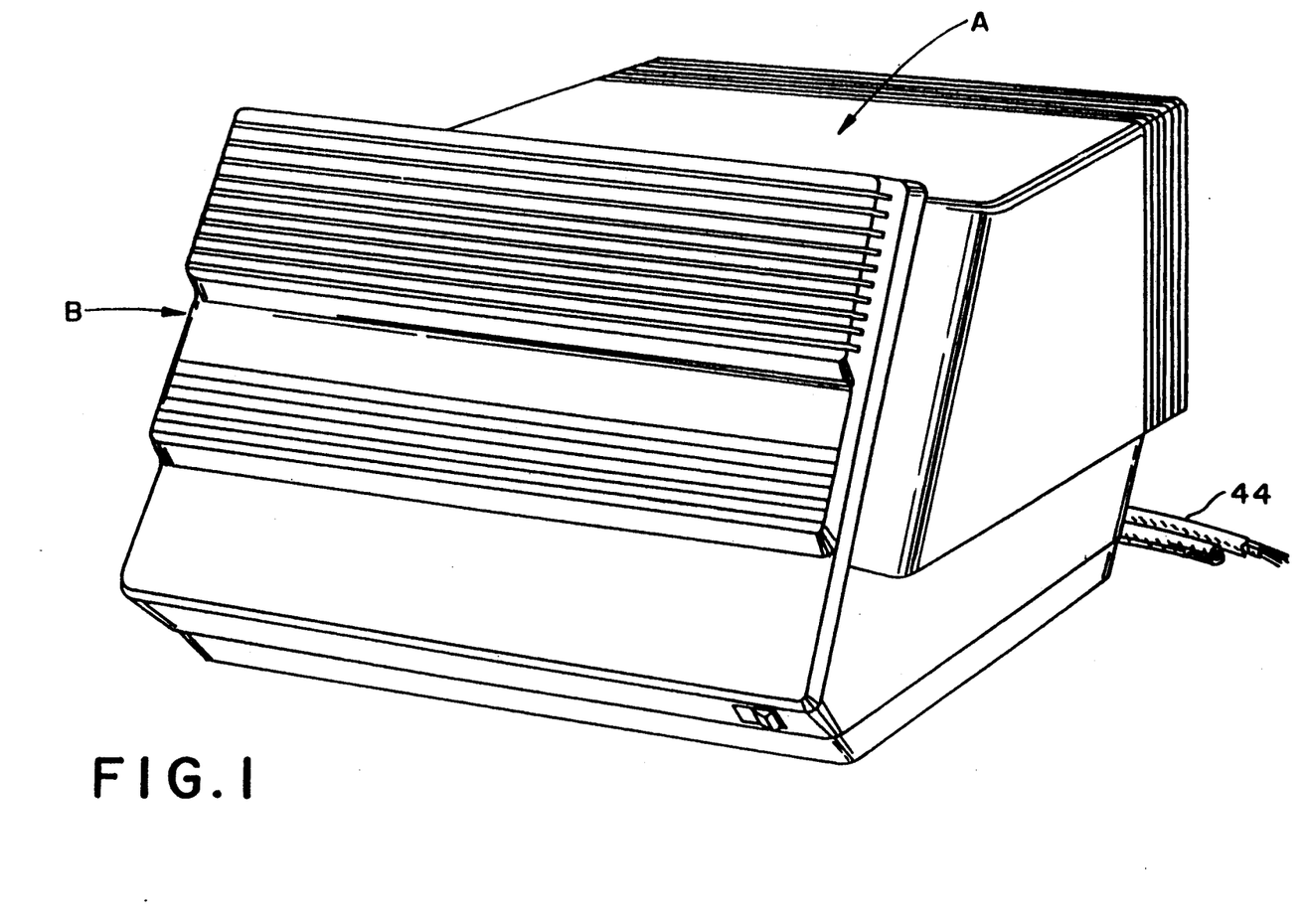
FIG. 1 is an exterior view of a counter top decontamination unit.
Figure 2:
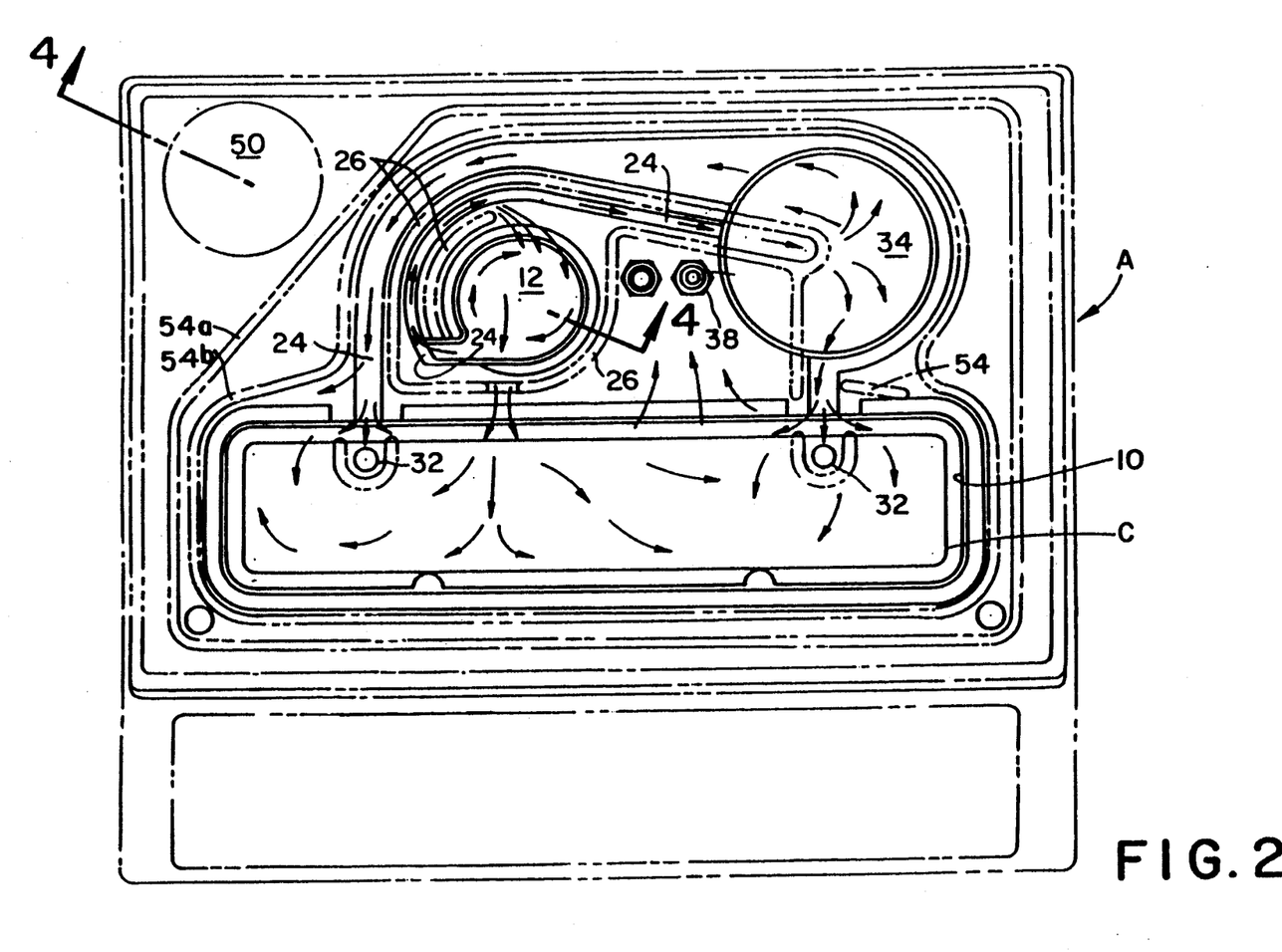
FIG. 2 is a front view of the decontamination unit with portions of the door shown in phantom.
Figure 3:
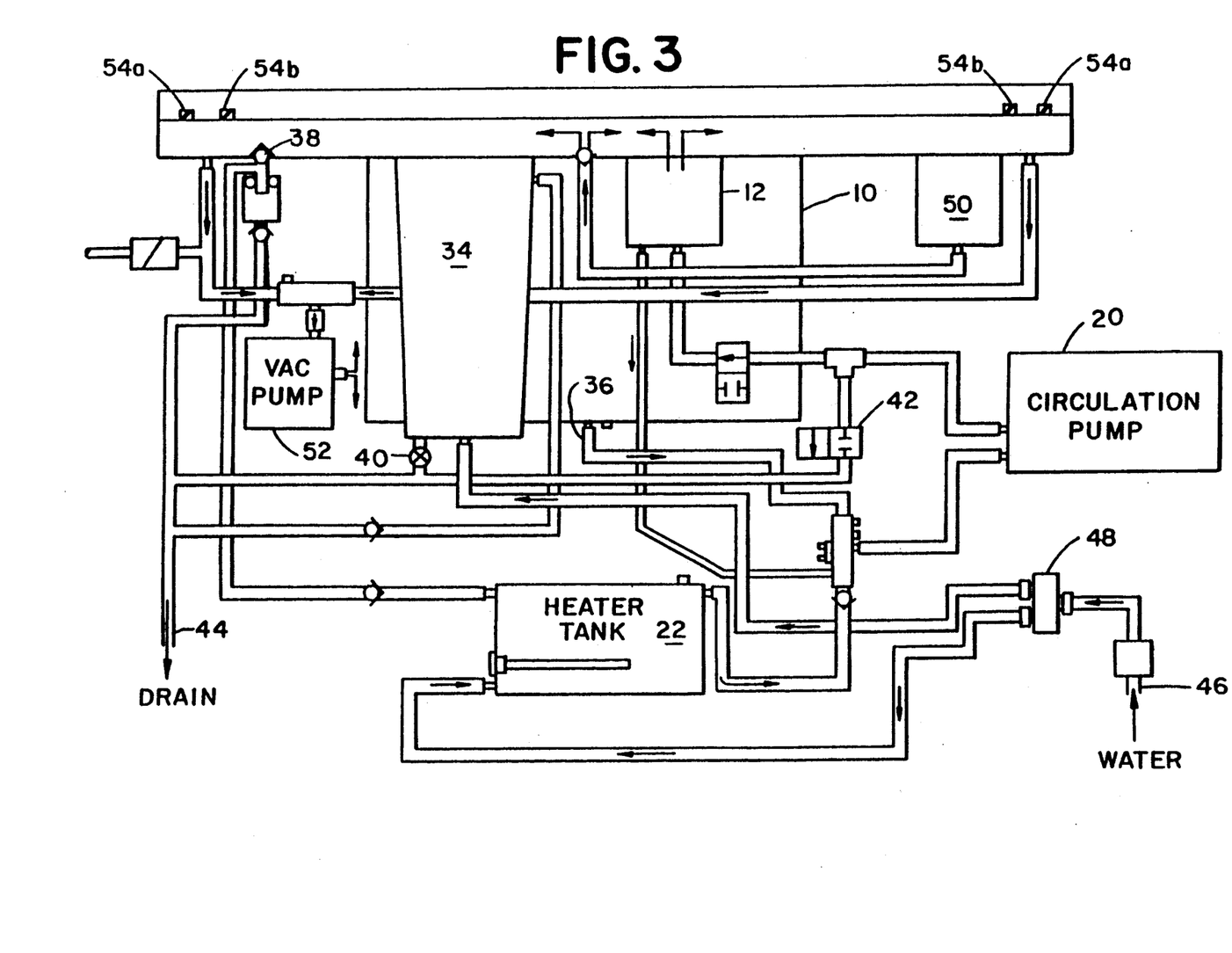
FIG. 3 is a plumbing diagram of the sterilizer of FIG. 1.

With reference to FIGS. 1, 2, and 3, a sterilizing apparatus A is configured to sit on a countertop or other convenient work surface. A front door B is manually openable to provide access for inserting a cartridge c holding items to be sterilized and at least a two chamber cup or package D for holding a decontaminant concentrate. More specifically, the items to be decontaminated are loaded in the cartridge C which is slidably received in a decontamination cartridge receiving well 10.

Figure 4:
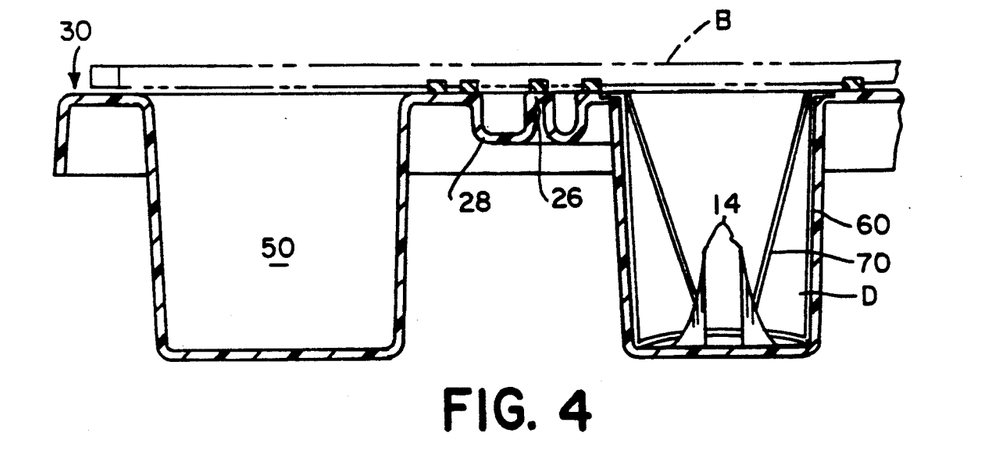
FIG. 4 is a detailed view of the sterilant concentrate cup receiving compartment of the decontamination unit of FIG. 1.

With particular reference to FIG. 4, as the cup D is loaded into a well 12, knives 14 pierce a base wall providing fluid access to its interior. A circulation pump 20 circulates heated water from a heater tank 22 through the cup and the cup receiving well 12 dissolving the reagents forming a liquid sterilant or other decontamination fluid. The decontamination fluid flows out a front opening of the well 12 into channels 24 defined by mating projections or gaskets 26 on the lid B and valleys 28 in a face plate 30. The decontamination fluid is channeled to receiving apertures 32 in the cartridge C and to a rinse liquid sterilizing filter 34. The sterilant which has flowed through the cartridge C flows out an outlet 36 of the cartridge receiving region 10 and is recirculated by the recirculation pump. All tubing and surfaces on a downstream side of the rinse fluid filter 34 are also sterilized. A one-way vent 38 in the space between the front door B and the face plate 30 allows excess decontaminant solution and air to overflow the drain 44.

After the items in the cartridge have been sterilized or otherwise decontaminated, valves 40, 42 are opened such that the sterilant or decontamination solution is drained through a drain 44. Water from an inlet 46 is either blocked, channeled by an inlet valve 48 to the heater tank 22 to start another cycle, or conveyed to the rinse fluid filter 34 to be sterilized. The filter removes particulates, bacteria, spores, and other pathogenic life forms and contaminants from the incoming water by size. By selecting the filter fine enough to remove all pathogenic life forms, a sterile rinse water or solution is created and circulated out an open end of the rinse filter and through the paths 24 defined between the cover B and the face plate 30. Other filters, anti-microbial means such as high intensity UV light, and the like, may be substituted for filter 34 to treat the rinse water. This rinse fluid is again channeled through the decontamination cartridge C and recirculated through the system. The rinse fluid is discharged through the drain 44 either at the end of a rinse cycle or continuously as new rinse fluid is introduced.

At the end of the rinse cycle, the rinse fluid is replaced with air which flows through a sterilizing filter 50 into the space between the cover and the face plate. The cover and face plate are held in a tight, fluid sealing relationship by a vacuum drawn by vacuum pump 52 in an annular gap defined between gaskets 54a, 54b which are received in one of the cover and the face plate.

In this manner, the sterilant solution sterilizes the rinse fluid sterilizing filter and all paths, passageways, and surfaces downstream from the filter 34. The prevents sterile rinse fluid from flowing over any surface which was not sterilized during the sterilizing portion of the cycle.

Figure 5:
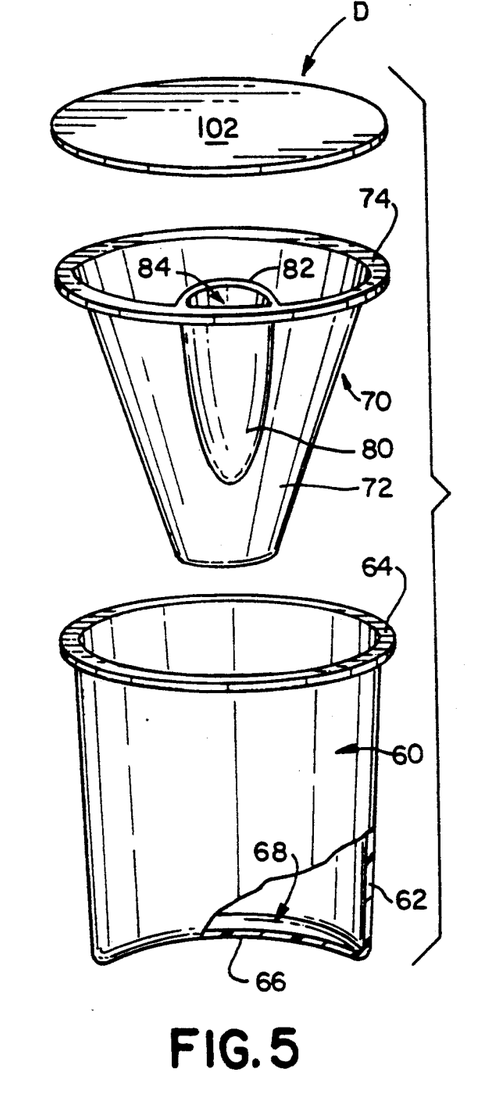
FIG. 5 is an exploded view of a two compartment cup in accordance with the present invention.

With reference to FIG. 5, the sterilant cup or package D includes a first or outer cup 60. The outer cup 60 includes a cylindrical peripheral wall 62 that has a flange 64 at a first, open end thereof. A base wall 66 closes a second, opposite end of the peripheral wall. The base wall has a central domed portion 68. The outer cup is constructed of a light weight polymeric material, such as a styrene plastic, which has sufficient resiliency that the dome 68 functions as a spring.

A second or inner cup portion 70 is received in the first cup portion 60. The second cup portion has a generally conical peripheral wall 72 that has a flange 74 integrally molded at a first, open end thereof. A base wall 76 closes a second end of the peripheral wall.

Figure 6:
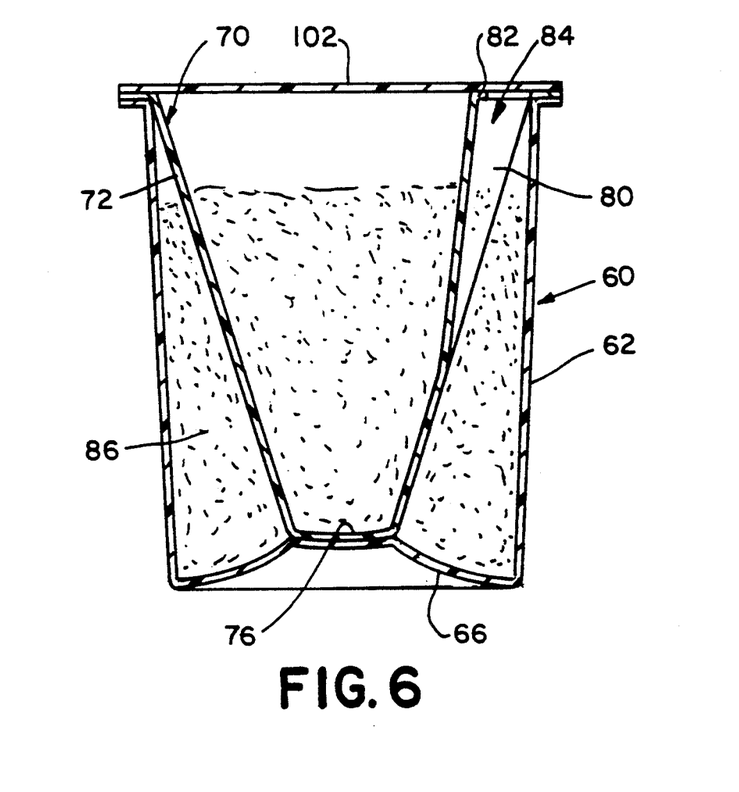
FIG. 6 is a side sectional view of a sealed two compartment cup filled with powdered reagents and ready for shipping.

With continuing reference to FIG. 5 and further reference to FIG. 6, the first and second cup portions are configured such that when the flanges 64, 74 are abutting and sealed together, the base walls 66, 76 abut and flex the dome 68 slightly. In this manner, the spring force of the dome 68 keeps the base walls of both containers in firm frictional engagement. Of course, either or both base walls can be domed. The base walls may be seated together. Appropriate sealing means for the flanges and the base walls include adhesive bonding, solvent welding, ultrasonic welding, or the like.

The peripheral wall 72 of the second cup portion has a recessed area or groove so that extends longitudinally therealong. An innermost surface of the recessed area extends generally parallel to the peripheral wall 62 of the first cup portion. A flange portion 82 is integrally formed in the same plane and has a continuous surface with the second cup portion flange 74. The flanges 74, 82 encircle and define a filling opening 84 in alignment with the recessed peripheral wall portion 80.

Preferably, the inner cup peripheral wall 72 is configured relative to the outer cup peripheral wall 62 such that an annular chamber 86 is defined therebetween. More specifically to the illustrated embodiment, the annular chamber 86 has substantially the same volume as the inner cup 70. Although various second cup peripheral wall designs may be utilized to achieve a selected relative volume ratio between the annular chamber and the second cup, the conical wall surface is preferred for its strength. When the cutters 14 enter the cup vertically from below, there is a tendency for one or both of the cups to collapse under the force of the cutter blade rather than being cut. The conical peripheral wall is a highly efficient cross-brace or trust-type arrangement which interacts with the outer cup to provide increased structural rigidity against vertical compression.

Figure 7:
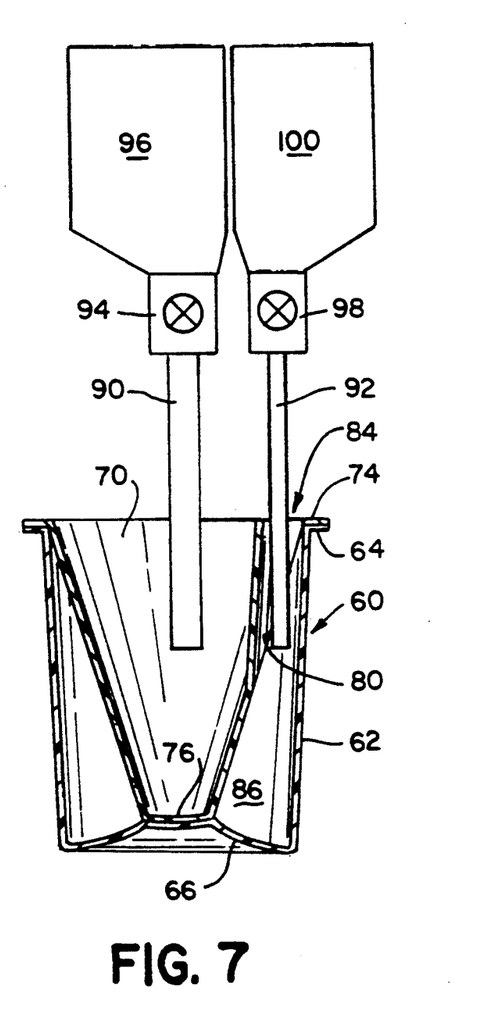
FIG. 7 illustrates filling of the two compartments of the cup of FIGS. 5 and 6.

With reference to FIG. 7, the inner cup 70 is inserted into the outer cup 60 with the dome 68 spring biasing the base walls together. The flanges 64, 74 and the base walls 66, 76 are connected together. To fill the annular chamber 86 and the second cup 70, the cup D is positioned below feed tubes 90 and 92 of a powdered material metering apparatus. Feed tube 90 is positioned in the inner cup 70 and extends to a metering valve 94 for dispensing a metered amount of a powdered reagent held in a reservoir 96. Analogously, feed tube 92 is received through the aperture 84 and in the recess so between the peripheral walls of the inner and outer cups. A second metering valve 98 meters a preselected volume of a second powdered reagent from a second reservoir 100.

With reference again to FIGS. 5 and 6, a closure 102 is adhered to the flanges 74 and 82 to seal the two chambers concurrently. In the preferred embodiment in which one of the powders liberates gas during storage, the closure 102 is a flexible layer of a permeable material. In other applications, the cover 102 may be a flexible sheet of impermeable foil, plastic, or the like. As yet another alternative, the closure 102 may be impermeable except for a small aperture or pin prick, a section of permeable material, or the like. This permits one of the chambers to be outgassed while retaining the other hermetically sealed from ambient humidity. As yet another alternative, the aperture ;84 may be sealed with an impermeable foil or the like and a permeable layer can then be adhered over the entirety of flange 74 such that the powdered reagent in the inner cup can breathe while the powdered reagent in the annular chamber is hermetically isolated from the ambient air. Optionally, the closure may include a pull tab to facilitate pealing off the closure for manual emptying of the contents.

In the preferred embodiment, the inner and outer cups each contain one of an acid precursor and a persalt. More specifically to the preferred embodiment, the acid precursor is acetylsalicylic acid and the persalt is sodium or other perborates. These two compounds react in the presence of water to form sodium metaborate, peracetic acid, and salicylic acid. The volume of powdered ingredients is selected relative to the volume of water such that a 0.2% W/V concentration of peracetic acid is achieved in the resultant decontamination solution. The sodium metaborate solution functions as an inorganic corrosion inhibitor and the salicylic acid is an organic corrosion inhibitor. Preferably, additional corrosion inhibitors, buffers, and a wetting agent are added to these powders. Preferred copper and brass corrosion inhibitors include azoles, benzoates, other five-membered ring compounds, benzotriazoles, tolytriazoles, mercaptobenzathiazole, and the like. Other anti-corrosive buffering compounds include phosphates, molybdates, chromates, dichromates, tungstates, vanidates, other borates, and combinations thereof. These compounds are effective for inhibiting steel and aluminum corrosion. For hard water in which calcium and magnesium salts may tend to precipitate, a sequestering agent such as sodium hexametaphosphate is also included. Other dry formulations can be utilized to generate chloride gas, hydrogen peroxide, hypochlorous acid, and other strong oxidants which have a biocidal effect.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A frangible, two compartment package for holding powdered reagents which interact in water to form an anti-microbial solution, the package comprising:
    an outer first cup portion having a first peripheral wall which has an opening at a first outer end and is closed by a first base portion at a first base end;
    an inner, second cup portion having a second peripheral wall, a flange means integrally connected at a second outer end of the second peripheral wall and a second base portion integrally connected to a second base end of the second peripheral wall, the first and second cup portions being configured such that the second cup portion flange means abuts and is sealed to the first cup portion first outer end and the first and second base portions are contiguous, the first and second peripheral walls being configured such that a first annular, powdered reagent receiving chamber is defined therebetween, the second cup portion defining a second chamber therein;
    a closure means which is selectively sealed to the second cup portion flange means closing the second chamber.

2. The package as set forth in claim 1 wherein the second cup portion peripheral wall has a longitudinally extending recess portion which mates with an aperture defined through the second cup portion flange means, whereby a filling tube is selectively receivable through the second cup flange aperture and along the recessed portion between the first and second cup portion peripheral walls for filling the annular chamber, the closure means being sealed to the flange means surrounding the aperture, whereby the first and second chambers are concurrently sealable.

3. The package as set forth in claim 2 wherein at least one of the first and second cup portion base portions has a dome arched toward the other; with the second cup portion flange means affixed to the first cup portion first end, the base portions abutting with sufficient force that the dome is flexed, such that a resiliency of the dome spring biases the first and second base portions into firm, frictional contact.

4. The package as set forth in claim 3 wherein the first peripheral wall is circularly cylindrical and is integrally connected with a flange means at the first outer end, the first and second cup portion flange means being coextensive and sealed together.

5. The package as set forth in claim 4 further including means for affixing the first and second base portions together.

6. The package as set forth in claim 4 wherein the second cup portion peripheral wall is substantially conical extending from the first cup portion peripheral flange means to a central portion of the first cup portion base portion for increasing the compressive strength thereof, whereby resistance to deformation on impact with a cutting tool is improved.

7. The package as set forth in claim 1 wherein one of the annular chamber and the second chamber holds an acid precursor and the other chamber holds a persalt.

8. The package as set forth in claim 7 wherein the acid precursor includes acetylsalicylic acid and the persalt includes sodium perborate.

9. The package as set forth in claim 8 wherein the closure means is a thin sheet of permeable material.

10. The package as set forth in claim 1 wherein at least one of the first and second cup portion base portions includes a dome arched toward the other; the second cup portion flange means being affixed to the first cup portion first end, the first and second base portions abutting with sufficient force that the dome is flexed, such that a resiliency of the dome spring biases the first and second cup portion base portions into firm, frictional contact.

11. The package as set forth in claim 1 wherein:
the first peripheral wall is circularly cylindrical; and,
the second cup portion peripheral wall is substantially conical extending from the first cup portion peripheral wall first end to a central portion of the first base portion or increasing the compressive strength thereof, whereby resistance to deformation on impact with a cutting tool is improved.

12. The package as set forth in claim 11 wherein the first and second cup portions are constructed of light weight plastic material.

13. The cup as set forth in claim 12 further including means for affixing the first and second base portions together.

14. The cup as set forth in claim 12 wherein the closure means is a thin sheet of permeable material.

15. A frangible, two compartment cup comprising:
a first cup portion having a second peripheral wall which has an opening at a first end and is closed by a first base wall at a second end;
a second cup portion having a second peripheral wall having a longitudinally extending recess, a flange integrally connected at a first, open end of the second peripheral wall, and a second base wall integrally connected to a second end of the second peripheral wall, the flange defining an aperture in communication with the longitudinally extending recess the first and second cup portions being configured such that the second cup portion flange abuts and is sealed to the first cup portion open end and such that an annular chamber is defined between the first and second cup portion peripheral walls, whereby a filling tube is selectively receivable through the flange aperture and along the recess between the first and second cup portion peripheral walls for filling the annular chamber;
at least one of the first and second cup portion base walls having a dome, the base walls abutting with sufficient force that the dome is flexed, such that a resiliency of the dome spring biases the first and second base walls into firm frictional contact;
a closure means which is selectively sealed to the second cup portion annular flange, whereby the second cup portion and the annular chamber are concurrently sealable.

16. A decontamination system comprising:
a powdered reagent cup receiving wall;
a means for defining a first fluid flow path between a water receiving inlet and the reagent cup receiving well to bring water from the inlet to the well to mix with powdered reagents and form a decontaminant solution;
a means for defining a second fluid flow path for the decontaminant solution from the reagent cup receiving well to a decontamination region for receiving items to be decontaminated;
a means for defining a third fluid flow path from the decontamination region of a drain outlet for selectively draining spent decontamination solution and rinse water;
a fluid circulating means for selectively circulating fluid through the first, second, and third fluid flow paths and among the inlet, the decontamination region, and the reagent cup receiving well;
a cutting blade means disposed adjacent and extending into the cup receiving well for cutting into at least two chambers of an at least two chamber powdered decontamination reagent holding cup;
the two chamber decontamination reagent holding cup including:
a first cup portion having a first peripheral wall which has an opening at a first end and is closed by a first base wall at a second end;
a second cup portion having a second peripheral wall having a longitudinally extending recess, a flange integrally connected at a first, open end of the second peripheral wall, and a second base wall integrally connected to a second end of the second peripheral wall, the flange defining an aperture in communication with the longitudinally extending recess, the first and second cup portion being configured such that the second cup portion flange abuts and is sealed to the first cup portion open end and such that an annular chamber is defined between the first and second cup portion peripheral walls, whereby a filling tube is selectively receivable through the flange aperture and along the recess between the first and second cup portion peripheral walls for filling the annular chamber;
at least one of the first and second cup portion base walls having a dome, the base walls abutting with sufficient force that the dome is flexed, such that a resiliency of the dome spring biases the first and second base walls into firm frictional contact;

a closure means which is selectively sealed to the second cup portion annular flange, whereby the second cup portion and the annular chamber are concurrently sealable.

17. The package as set forth in claim 16 wherein one of the annular chamber and the second cup portion holds an acid precursor and the other holds a persalt.

18. The package as set forth in claim 17 wherein the acid precursor includes acetylsalicylic acid and the persalt includes sodium perborate.

19. A method comprising providing a first cup which includes a first cup having a first peripheral wall which has an opening at a first end and is closed by a first base wall at a second end;

inserting a second cup into the first cup which second cup includes: a second peripheral wall, a flange integrally connected at a first, open end of the second peripheral wall, and a second base wall integrally connected to a second end of the second peripheral wall, the second cup peripheral wall having a vertically extending recess which mates with an aperture defined through the second cup flange, the first and second cups being configured such that when the second cup is inserted into the first cup until the second cup flange abuts the first cup open end, the base walls are contiguous, the first and second cup peripheral walls being configured such that an annular, powdered reagent receiving chamber is defined therebetween;

sealing the second cup flange to the first cup first end;

inserting a first filling tube through the flange aperture into the annular chamber and metering a preselected volume of a first powdered reagent into the annular chamber;

inserting a second filling means into the second cup and metering a preselected volume of a second powdered reagent thereinto;

sealing a closure to the second cup flange surrounding the second cup and the annular chamber filling aperture such that the first and second chambers are sealed concurrently.

20. The method as set forth in claim 19 further including:

conveying the sealed cups and the contained powdered reagents to a site at which decontamination is to be performed;

concurrently piercing the first and second base walls of the first and second cups;

mixing the first and second powdered reagents with water to form a decontamination solution;

immersing items to be decontaminated in the decontamination solution.

21. The method as set forth in claim 20 wherein the powdered reagents in one of the second cup and the annular chamber include an acid precursor and the powdered reagents in the other include a persalt.

22. The method as set forth in claim 21 wherein the acid precursor includes acetylsalicylic acid and the persalt includes sodium perborate.

* * * * *